(12) United States Patent
Niederlöhner et al.

(10) Patent No.: US 10,175,323 B2
(45) Date of Patent: Jan. 8, 2019

(54) ADAPTING ACTIVATION PARAMETERS USED TO GENERATE A PULSE SEQUENCE WHEN ACTIVATING A MAGNETIC RESONANCE SYSTEM

(71) Applicants: Daniel Niederlöhner, Erlangen (DE); Dominik Paul, Bubenreuth (DE); Jörg Roland, Hemhofen (DE)

(72) Inventors: Daniel Niederlöhner, Erlangen (DE); Dominik Paul, Bubenreuth (DE); Jörg Roland, Hemhofen (DE)

(73) Assignee: Siemens Aktiengesellschaft, München (DE)

( * ) Notice: Subject to any disclaimer, the term of this patent is extended or adjusted under 35 U.S.C. 154(b) by 919 days.

(21) Appl. No.: 14/616,471

(22) Filed: Feb. 6, 2015

(65) Prior Publication Data
US 2015/0219736 A1 Aug. 6, 2015

(30) Foreign Application Priority Data
Feb. 6, 2014 (DE) .......................... 10 2014 202 183

(51) Int. Cl.
| | | |
|---|---|---|
| G01R 33/54 | (2006.01) | |
| A61B 5/055 | (2006.01) | |
| G01R 33/385 | (2006.01) | |
| G01R 33/28 | (2006.01) | |

(52) U.S. Cl.
CPC ............ G01R 33/543 (2013.01); A61B 5/055 (2013.01); G01R 33/288 (2013.01); G01R 33/385 (2013.01)

(58) Field of Classification Search
CPC ................................................ G01R 33/3664
USPC ......................................................... 324/322
See application file for complete search history.

(56) References Cited

U.S. PATENT DOCUMENTS

| | | | | |
|---|---|---|---|---|
| 8,224,609 | B2* | 7/2012 | Griswold | G01R 33/5612 702/106 |
| 2003/0098688 | A1* | 5/2003 | Brinker | G01R 33/583 324/309 |
| 2007/0010737 | A1 | 1/2007 | Harvey et al. | |
| 2007/0024283 | A1* | 2/2007 | Bielmeier | G01R 33/288 324/314 |
| 2015/0219739 | A1* | 8/2015 | Brinker | G01R 33/583 324/309 |

FOREIGN PATENT DOCUMENTS

| | | |
|---|---|---|
| DE | 19913547 A1 | 11/1999 |
| DE | 602004009052 T2 | 6/2008 |

OTHER PUBLICATIONS

German Office Action for German Application No. 10 2014 202 183.9, dated Oct. 6, 2014, with English Translation.

* cited by examiner

*Primary Examiner* — Susan S Lee
(74) *Attorney, Agent, or Firm* — Lempia Summerfield Katz LLC

(57) ABSTRACT

A method for adapting activation parameters used to generate a pulse sequence when activating a magnetic resonance system is provided. The method includes determining stimulation values for the pulse sequence based on predefined activation parameters. The stimulation values represent a stimulation exposure of a patient. Test regions that exhibit stimulation maxima are identified in the pulse sequence, and the identified test regions are tested with respect to compliance with a predefined stimulation limit value.

15 Claims, 7 Drawing Sheets

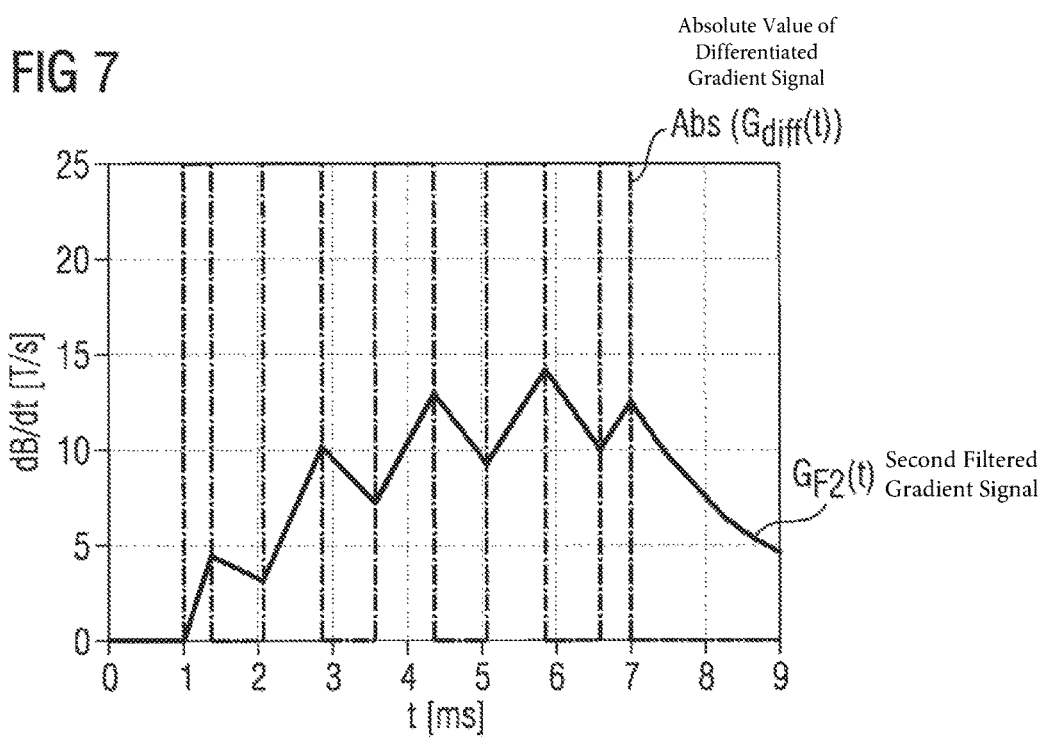
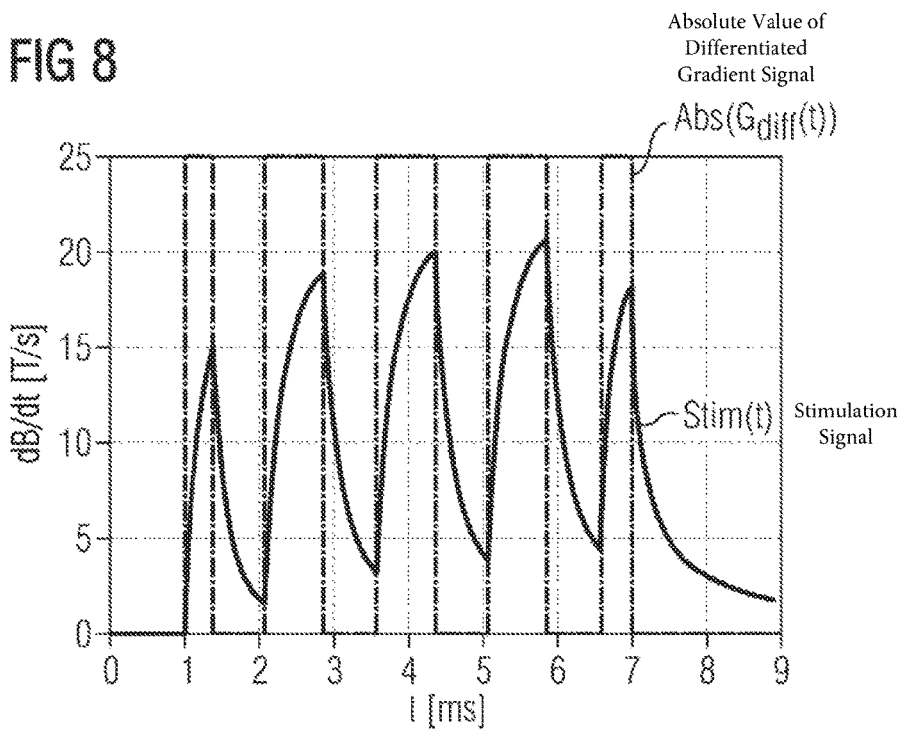

ADAPTING ACTIVATION PARAMETERS USED TO GENERATE A PULSE SEQUENCE WHEN ACTIVATING A MAGNETIC RESONANCE SYSTEM

This application claims the benefit of DE 10 2014 202 183.9, filed on Feb. 6, 2014, which is hereby incorporated by reference in its entirety.

BACKGROUND

The present embodiments relate to adapting activation parameters that are used to generate a pulse sequence when activating a magnetic resonance system.

In the case of known nuclear spin resonance devices, rapidly switched gradient fields of high amplitude are superimposed on a basic magnetic field. As a result of the switching of gradient pulses, the patients may be stimulated by magneto-stimulation in the context of MR examinations. Both humans and animals are considered to be patients in the following. The stimulations are caused by the effect of an electric field on the patient. The electric field in this case is induced by the magnetic flux $\phi=\int BdA$, which is generated by each of the three gradient coils as per the Maxwell equations, where B is the magnetic flux density, and A is the area through which the magnetic flux flows. For a specific nuclear spin resonance device, the magnitude of the electric field induced by the switching of a gradient coil is directly proportional to the time-relative change in the magnitude of the magnetic flux $\Phi$ and, in the case of a constant flow-through area, also proportional to $$\frac{d|B|}{dt}$$

(e.g., the time-relative derivation of the magnitude of the magnetic field produced by the gradient coil). Due to the proportionality of electric field and $$\frac{dB}{dt}$$

(the time-relative change in the magnetic flux density B), it is sufficient to examine the time-relative variation of the magnetic flux density B. As a result of the proportionality of magnetic flux density B and the gradient field G for a given gradient coil, an examination of the time-relative change $$\frac{d}{dt}$$

of the location-dependent gradient field G (generally specified in mT/m) is equivalent to the aforementioned examination of the time-relative change $$\frac{d}{dt}$$

of the location-dependent magnetic flux density B (mT). The time-relative variation of the gradient signals is therefore examined in the following. A stimulation occurs when a characteristic threshold value of the electric field is exceeded. For a fixed gradient model, the corresponding threshold value of $$\frac{dB}{dt} \text{ or } \frac{dG}{dt}$$

depends on the anatomy and the physiology of the patient, the orientation of the patient in the nuclear spin resonance device, and the geometric and physical properties of the three gradient coils.

$$\frac{dB}{dt}$$

is given by the amplitude of the gradient pulses and the switching times (rise time). However, in practice, the gradient model is not constant in terms of either the amplitudes or the timing but, in addition to the choice of the measurement sequence to be used, depends, for example, on the chosen measurement parameters (e.g., layer thickness, number of layers, field of view (FOV), matrix sizes, repetition time (TR), echo time (TE), etc.). In this case, in addition to the above cited parameters, the threshold value for the stimulation also depends, for example, on the time-relative structure of the individual gradient pulses, the total number thereof, their repeat rate, and the superimposition of all three gradient coils $G_x$, $G_y$, and $G_z$.

In the case of whole-body gradient coils, the stimulation is influenced not only by the $B_z$ component of the magnetic flux, which runs in a longitudinal direction, but also by transverse components $B_x$ and $B_y$. The $B_y$ component is more critical with regard to stimulations since the field lines penetrate the body from the front. Consequently, in the case of a supine or prone position of the patient, the stimulation limit value is to be smallest for the y-axis. In terms of physiology, a stimulation that is performed deliberately using an external electric field may be described very simply in two steps. In this case, the electric field may either act directly from the outside, or be induced by a changing magnetic field.

In a first step, the electric field generates an electric potential at the cell wall of the stimulated nerve cell. The cell wall of the nerve cell may almost be imagined as a capacitance that is charged by the electric field. When the electric potential exceeds a characteristic threshold value, an action potential is triggered in the nerve cell and diffuses over the whole nerve cell. In a second step, at the junction of two nerve cells (e.g., the synapses), an action potential on the pre-synaptic side results in the spilling out of chemical messenger substances (e.g., neurotransmitters). These substances are absorbed on the post-synaptic side (e.g., in the next nerve cell) and trigger a further action potential there. The stimulus diffuses. In this case, the concentration of the messenger substances in the synapse is a measure of the number of action potentials triggered on the post-synaptic side. For example, the concentration of the messenger substances in the synapse only decreases slowly. The characteristic time constant lies in the region of a few milliseconds.

In order to monitor and check the stimulation produced by the magnetic fields of the gradient coils, use is made of look-ahead systems (also referred to as a stimulation checking unit in the following) and realtime monitoring systems (also referred to as a stimulation monitoring unit or realtime monitoring unit in the following). The stimulation checking units may be implemented as a software module and configured such that, when generating pulse sequences, the parameters of the pulse sequences are so adjusted that the stimulation caused by the pulse sequences does not exceed a limit value. In this case, the stimulation checking units also calculate in advance the expected stimulation of a pulse sequence that is generated by a pulse sequence generating unit. If the anticipated stimulation caused by the pulse sequence is below a limit value, the stimulation checking unit outputs a proposal to the pulse sequence generating unit, indicating the activation parameters to be selected for the pulse sequence in order to avoid exceeding the limit value but obtain an optimal imaging result. If the anticipated resulting stimulation caused by the pulse sequence exceeds a limit value, the stimulation checking unit instructs the pulse generating unit to generate a new pulse sequence using different activation parameters. The realtime monitoring systems or stimulation monitoring units may be configured as fixed hardware systems or as digital signal processors with a Harvard architecture, for example, since the process performed by the realtime monitoring systems is very time-critical. A system that is implemented purely as software may be inferior to the hardware systems or digital signal processors in terms of computing speed. The realtime monitoring systems monitor the applicable gradient signals at the gradient coils during the operation of the magnetic resonance system and determine, from the measured physical variables (e.g., the coil voltage and/or the coil current), the stimulation that is generated in each case by the magnetic fields of the gradient coils. If the stimulation exceeds a predefined limit value, the imaging process or sampling process of the magnetic resonance system is terminated immediately in order to prevent excessive exposure of the patient.

The calculation of the stimulation by the stimulation checking units is conventionally only performed for those time segments, of the pulse sequence to be generated, in which the strongest stimulations are expected to occur. The identification of these regions is conventionally performed in advance using the previously known properties of the series of gradient pulses. Depending on the sequence, the identification of these regions may, however, be very difficult and uncertain. In practice, the gradient model is not constant with respect to either the amplitudes or the timing, but, in addition to the choice of the measurement sequence to be used, depends, for example, on the chosen measurement parameters (e.g., layer thickness, number of layers, field of view (FOV), matrix sizes, repetition time (TR), echo time (TE), etc.). The pulse segment having the phase coding step with the strongest gradients may be determined when using, for example, a, SPC sequence, yet the greatest stimulation need not occur in this segment since the stimulation at a specific time point is also dependent on the values of the gradient pulses before and after the cited time point. For example, if the method of flexible reordering is used for an SPC sequence (e.g., the sampling points in the k-space are ideally completed in the automatic mode), or even compressed sensing, the identification of this region is not reliable and depends on many protocol parameters such as, for example, the matrix size, the resolution or the acceleration factor. In addition to the SPC sequence, the cited problems also arise in the case of other sequences (e.g., 3D sequences such as Vibe or TFL). If the pulse segment with a stimulation to be calculated in advance is now enlarged or even extended to include the whole region of the pulse sequence in order to obtain a more reliable result, this would result in very long computing times when using the conventional method as outlined above to calculate the proposal for the activation parameters for a pulse sequence that is to be generated. The resulting time excess is difficult for the operator to accept and is also prevented by the system, since a time limit of 30 s may be set for the individual pulse sequence in order that the process remains tolerable for the operator. However, this provides that the activation parameters used in such a case will with a certain degree of probability generate either a pulse sequence that results in termination by the realtime monitoring system due to unacceptably high stimulation values, or a pulse sequence that would not exceed the stimulation limit value of the patient, which is always defined individually. However, in such a case, the quality of the recorded image may not be optimal, since a pulse sequence that is only just compatible would not be chosen, and there would be a correspondingly significant distance from the maximal compatible stimulation values. Therefore, when using the conventional methods for adapting the activation parameters of a pulse sequence, the problem occurs either that it is not possible to reliably predict whether the stimulation produced in the body of the patient by the pulse sequence will not exceed the predefined limit value, or that the total time of the adaptation process is too long and therefore a less than optimal image result is accepted. In order to overcome or at least slightly lessen the cited problems, provision was previously made, when defining the pulse sequence segments where stimulation is to be calculated, for selecting time intervals or pulse sequence segments that are as long as possible but are still just short enough to remain below the cited time limit for a pulse sequence of 30 s. When determining whether the stimulation produced by the pulse sequence to be generated was still within the predefined stimulation limit value, a tolerance factor was taken into consideration due to the uncertainty that also remained in this case. As before, when using this approach, the selection of pulse sequence segments where stimulation values are calculated is again effected heuristically or according to a criterion that is adversely affected by some uncertainty that the correct region of the pulse sequence is likely to be chosen. As a result of the tolerance factor, the calculation often results in stimulation values that are too high in comparison with the real stimulation values, thereby unnecessarily reducing the output and hence the effectiveness of the pulse sequence that is used. As a result, even when using this optimized approach, negative effects on the measurement time or the image quality may not be prevented. There is even the risk that the image recording may be terminated in the event that, contrary to expectations, the cited tolerance factor was set too low, or incorrect pulse sequence segments were selected for the stimulation value calculation, consequently resulting in sequence terminations at runtime by the stimulation monitoring unit or the realtime monitoring unit as part of the realtime monitoring or online monitoring.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an alternative adaptation of activation parameters that are used to generate a pulse sequence when activating a magnetic resonance system is provided.

In one embodiment of a method, stimulation values for the pulse sequence are first determined based on predefined activation parameters. The stimulation values represent the stimulation exposure of the patient. With reference to the determined stimulation values, test regions are identified based on the stimulation values of the pulse sequence. The identified test regions are tested with respect to corresponding compliance with a predefined stimulation limit value.

The determination of the stimulation values may, for example, be performed such that a stimulation curve is determined or calculated for the generated pulse sequence. Alternatively, however, the determination may be restricted to determining a smaller number of stimulation values (e.g., just one or two values in the extreme case). The test regions are the segments of the pulse sequence that are to be tested with respect to exceeding a stimulation limit value. Unlike the conventional method, the critical regions or the test regions of the pulse sequence are not defined in advance based on heuristic criteria, but a decision with respect to the selection and the dimension of the test regions is only made after the stimulation values assigned to the pulse sequence have been determined. In this case, the determination of the stimulation values may be done using estimation based on a model, or, more precisely, by a calculation of the stimulation values, in which the effect of the change in the magnetic flux caused by the pulse sequence, and its physiological effects, are taken into consideration in the form of a model. This provides that the regions of the pulse sequence in which excessive stimulation values unexpectedly occur are taken into consideration when determining the stimulation values. After determination of the stimulation values, a narrower selection of the test regions may be made because, based on the determination of the stimulation values assigned to the pulse sequence, it is possible to predict with far greater precision the segment of the pulse sequence in which the highest stimulation values or stimulation maxima are found. This consequently results in a significantly shorter process time for both the verification of compliance with a stimulation limit value and the calculation of a proposal for the activation parameters of a pulse sequence to be generated.

The device of one or more of the present embodiments for determining activation parameters used when activating a magnetic resonance system includes a stimulation checking unit including a stimulation value determination unit. The device also includes a test region identification unit and a stimulation test unit. The stimulation value determination unit is configured to determine the stimulation values for a pulse sequence based on predefined activation parameters. The stimulation values represent the stimulation exposure of the patient. The test region identification unit is configured to determine test regions based on the stimulation values of the pulse sequence, and the stimulation test unit is configured to verify the identified test regions with respect to compliance with a predefined stimulation limit value.

The cited units may be implemented as software modules. A subset of the cited units (e.g., the stimulation value determination unit and the stimulation test unit) may be implemented as software modules. Alternatively, the cited units may be implemented as hardware (e.g., one or more processors).

In the following, activation parameters may be all of the variables that are adjusted when generating a gradient pulse sequence and setting or modification of which influences the gradient pulse sequence, which is also referred to simply as pulse sequence below.

In the case of an SPC sequence, for example, the test region that is determined may be a single echo train. In the case of sequences that are characterized by homogeneity (e.g., sequences that do not vary significantly over time), the pulse sequences may be divided into N subregions of identical size, for example, and the corresponding subregion in which the maximal stimulation was determined may then be marked.

Unlike conventional arrangements, the device of one or more of the present embodiments therefore has a test region identification unit that is connected behind the stimulation value determination unit, for example. By virtue of the stimulation values being calculated in advance by the stimulation value determination unit, the test region identification unit may estimate very accurately which pulse sequence segments hold the highest stimulation values, or the maxima of the stimulation values in a specific embodiment. With higher prediction reliability, a narrower selection of the test regions may be made. This results in a time saving when calculating a proposal with respect to the activation parameters assigned to the pulse sequences to be generated, since only the stimulation values assigned to the cited narrower segments are to be taken into consideration when calculating the proposal in this case.

The pulse sequence signal tested by the device may then be sent to a realtime monitoring unit. In this case, the realtime monitoring unit is configured to receive a pulse sequence that has been tested by the cited device, and to test the pulse sequence in real time with respect to compliance with a predefined stimulation limit value. If the stimulation limit value is observed, the realtime monitoring unit transfers the tested pulse sequence to a pulse sequence amplification unit, and if the stimulation limit value is not observed, the sampling process of the magnetic resonance system is terminated.

Since the monitoring of the stimulation takes place in real time and is therefore very time-critical, the realtime monitoring unit may be configured as a hardware system or as a digital signal processor.

The control apparatus of one or more of the present embodiments includes a device and a pulse sequence code generating unit configured to generate a pulse sequence code for a pulse sequence generating unit without defining critical regions for the stimulation testing.

The pulse sequence code generating unit differs from a conventional pulse sequence code generating unit in that the pulse sequence code generating unit does not define any critical regions for the stimulation testing.

The magnetic resonance tomography system includes the device. In this case, the device for determining activation parameters used when activating a magnetic resonance system may be implemented as software. However, the previously described realtime monitoring unit and the pulse sequence amplification unit may be embodied as hardware, possibly making use of specific signal processors or amplifier circuits.

The device, the control apparatus and the magnetic resonance system may also be developed in a similar manner to that specified with the method.

According to an embodiment of the method, if the stimulation limit value is exceeded in a test region, a modified pulse sequence for at least this test region is generated using new activation parameters, the stimulation values for the modified pulse sequences in the test region are determined, and the test region is tested with respect to compliance with a predefined stimulation limit.

Therefore, after a pulse sequence has been classified as unsuitable in a test region, a new pulse sequence is generated for at least this test region. Unlike the procedure for the first pulse sequence, in which the stimulation values were calculated over a wide region (e.g., the whole region of the pulse sequence), an embodiment provides for determining the stimulation values for only those regions or test regions determined as critical in the first pulse sequence. Additional process time is therefore saved, thereby offering greater operator convenience and allowing increased effort and hence greater accuracy when determining the stimulation values and calculating the proposal.

According to one variant of the method, before the generation of the new activation parameters, a proposal calculation of the activation parameters is performed based on the predefined stimulation limit value and the stimulation values that have been determined for the identified test regions.

The new pulse sequence may therefore be generated by a systematic procedure based on the existing data.

Following completion of the described method, if the determined stimulation values do not exceed a predefined limit value, the determined activation parameters or the pulse sequence assigned to the activation parameters may be supplied to an activation unit of the magnetic resonance system.

The activation unit may increase the amplitude of the pulse sequence, for example. Realtime monitoring of the stimulation may also be performed. The signal assigned to the pulse sequence is applied at the gradient coils.

In an alternative embodiment of the method, before the activation parameters are supplied to the activation unit of the magnetic resonance system, a proposal calculation of the activation parameters is performed based on the predefined stimulation limit value and the maximal stimulation values that have been determined for the identified test regions.

The proposal calculation makes it possible to verify that in terms of stimulation values, the pulse sequence that has been classified as suitable does not, for example, lie significantly below the permitted region (e.g., significantly below the stimulation limit value), such that an output or effectiveness is consequently reduced with regard to the imaging or the image quality. The activation parameters may therefore be determined or calculated as a function of the stimulation values that have been determined for the pulse sequence and the stimulation limit value. A feedback signal is provided to indicate not only that the stimulation value has been exceeded, but also the extent to which the stimulation value has been exceeded, and a corresponding response.

According to an embodiment of the method, the determining of the stimulation values may be realized by calculating values representing the stimulation based on the pulse sequence.

According to an embodiment of the method, the calculation may be performed in accordance with the following formula:

$$Stim(t) = a_1 \cdot abs\left(\frac{d}{dt}G(t) \otimes f_{F1}(t)\right) \oplus a_2 \cdot abs\left(\frac{d}{dt}G(t)\right) \otimes f_{F2}(t)$$

In this case, Stim(t) is the stimulation function to be determined, G(t) is the gradient signal, d/dt G(t) is the first time-relative derivation of the gradient signal, subsequently also referred to as $G_{diff}(t)$, $f_{F1}(t)$ is a first filter function, $f_{F2}(t)$ is a second filter function, and $a_1$ and $a_2$ are weighting factors. The operator $\otimes$ is a convolution operator, and the operator $\oplus$ represents a composition. According to an embodiment, the composition may be an addition.

For example, the first derivation $G_{diff}(t)$ of the pulse sequence is calculated. A first filtered gradient signal $G_{F1}(t)$ is calculated by convolution of the first derivation $G_{diff}(t)$ of the pulse sequence with a first filter function $f_{F1}(1)$. The absolute values abs($G_{F1}(t)$) of the filtered first derivation $G_{F1}(t)$ of the pulse sequence are calculated. The absolute values of the first derivation $G_{diff}(t)$ are also calculated, and a second filtered gradient signal $G_{F2g}(t)$ is calculated by convolution of the absolute values abs($G_{diff}(t)$) of the first derivation $G_{diff}(t)$ with a second filter function $f_{F2}(t)$. The first filtered gradient signal $G_{F1}(t)$ is multiplied by a first weighting factor $a_1$, and the second filtered gradient signal $G_{F2}(t)$ is multiplied by a second weighting factor $a_2$. The first weighted filtered gradient signal $G_{F1g}(t)$ and the second weighted filtered gradient signal $G_{F2g}(t)$ are composed, or added in the case of a particular embodiment, and the result thereof reveals the above cited stimulation function Stim(t).

In an effective embodiment of the method, as part of the act of determining the stimulation values, first the time intervals between the individual pulses of the pulse sequence are determined, the amplitudes of the individual pulses of the pulse sequence are determined, the quotients are determined from the time intervals and the amplitude of the respective pulse sequence, and whether the quotients exceed a predefined limit value is tested. If a quotient exceeds the limit value, it is assumed that the pulse assigned to this quotient causes a stimulation, and the stimulation for this pulse is determined. This may take place in accordance with the computing method outlined above, for example. It is therefore only necessary to calculate the stimulation for some of pulses in the pulse sequence, thereby further shortening the process time.

As part of the act of determining the stimulation values, provision may also be made for first determining the time intervals between the individual pulses of the pulse sequence, and then defining the test regions in the pulse sequence segments where a predefined minimal time interval between two pulses is not reached. The stimulation values for the defined test regions are subsequently to be determined.

The predefined minimal time interval may be determined as a function of the maximal time-relative change in the gradient pulses of the pulse sequence, also known as the slew rate, for example.

According to an embodiment of the device, the device includes a pulse sequence generating unit configured to generate a pulse sequence. The pulse sequence generating unit is configured such that, if it is determined that a predefined stimulation limit value is observed, the pulse sequence is transferred to an activation unit; if it is determined that a predefined stimulation limit value is not observed, a new pulse sequence is generated using new activation parameters and only the pulse sequence segments in the identified test region are supplied to the stimulation checking unit.

Therefore, after a pulse sequence has been classified as unsuitable, a new pulse sequence is generated by the pulse sequence generating unit. Unlike the procedure for the first pulse sequence, the pulse sequence generating unit supplies the pulse sequence segments in the identified test region to the stimulation checking unit.

For example, the stimulation value determination unit of the device may be configured such that, if the stimulation limit value is exceeded, the stimulation values are determined for a pulse sequence that has been newly generated by the pulse sequence generating unit using new activation parameters for the identified test regions, and the stimulation test unit may be configured such that the identified test regions are tested again with respect to compliance with a predefined stimulation limit value.

According to an embodiment of the device, the stimulation checking unit or the stimulation value determination unit contained in the stimulation checking unit is configured such that the stimulation values are no longer determined over a wide region (e.g., the whole region) of the pulse sequence, and the stimulation values are instead only determined for the critical regions or test regions determined in the context of the first pulse sequence. Therefore, once the test region has been determined, the test region does not have to be determined again in the context of the subsequent passes. For example, it is also not necessary to determine the stimulation values outside of the test region again. Additional process time is therefore saved, thereby offering greater operator convenience and allowing increased effort and hence greater accuracy when determining the stimulation values and calculating the proposal.

The device may include a proposal calculation unit configured to perform, before the generation of the new activation parameters, a proposal calculation of the activation parameters based on the predefined stimulation limit value and the stimulation values that have been determined for the identified test regions.

Alternatively or additionally, the device may also include a proposal calculation unit configured to perform, before the transfer of a pulse sequence to an activation unit of the magnetic resonance system, a proposal calculation of the activation parameters based on the predefined stimulation limit value and the maximal stimulation values that have been determined for the identified test regions. The proposal calculation unit may therefore help to verify that in terms of stimulation values, the pulse sequence that has been classified as suitable does not, for example, lie significantly below the permitted region (e.g., significantly below the stimulation limit value), such that its output or effectiveness is consequently reduced with regard to the imaging or the image quality. The activation parameters may therefore be determined or calculated as a function of the stimulation values that have been determined for the pulse sequence and the stimulation limit value. The proposal calculation unit may be part of the pulse sequence generating unit or also part of the stimulation checking unit.

BRIEF DESCRIPTION OF THE DRAWINGS

FIG. 7 graphically illustrates exemplary absolute values of a gradient signal $G_{diff}(t)$ and a corresponding filtered gradient signal $G_{F2}(t)$;

FIG. 8 graphically illustrates an exemplary stimulation function Stim(t) and the absolute values of a gradient signal $G_{diff}(t)$;

DETAILED DESCRIPTION

Figure 1:
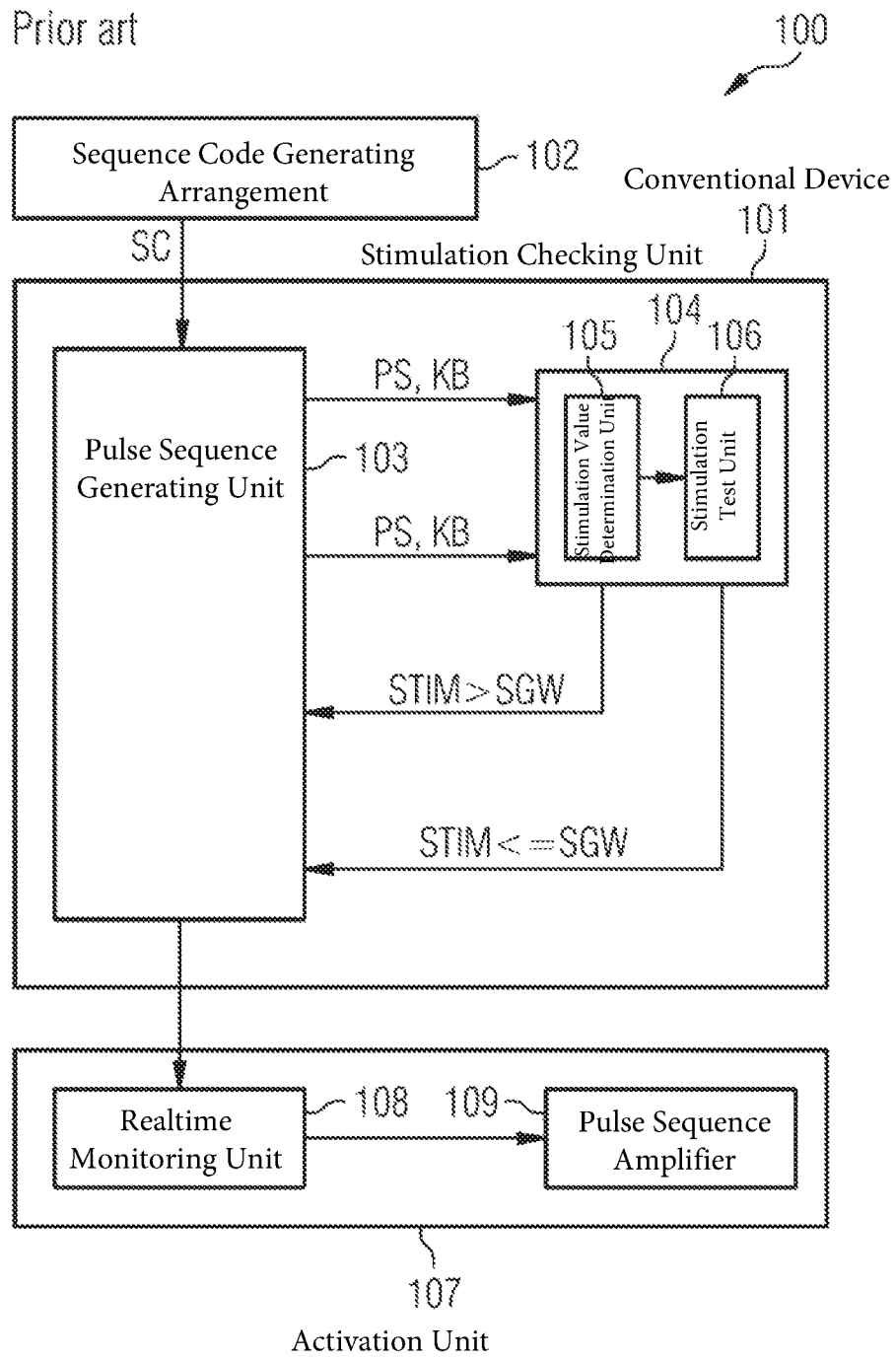
FIG. 1 shows a schematic illustration of a control apparatus of the prior art.

FIG. 1 schematically shows the structure of a control apparatus 100. The control apparatus 100 includes a conventional device 101 for generating a pulse sequence PS and for adapting an activation parameter that is used to generate the pulse sequence PS. The control apparatus 100 includes an activation unit 107 (e.g., an MR scanner) that includes a realtime monitoring arrangement 108 (e.g., a stimulation monitoring unit) and a pulse sequence amplifier 109 (e.g., a gradient amplifier). The sequence code generating arrangement 102 generates a pulse sequence code SC and defines the critical pulse sequence segments KB for which the maximal stimulation values are expected. The stimulation values are caused by the pulse sequence that is to be generated. A pulse sequence generating unit 103 creates a pulse sequence PS or a pulse train and supplies the critical region KB or the critical pulse sequence segment (e.g., the signal amplitude values assigned to the critical pulse sequence segment) to the stimulation checking unit 104. The stimulation checking unit 104 includes a stimulation value determination unit 105 and a stimulation test unit 106. The stimulation value determination unit 105 determines the stimulation values STIM assigned to the received pulse sequence segment. The calculated values are then sent to the stimulation test unit 106. This tests whether the transferred stimulation values exceed a predefined limit value. If the transferred stimulation values exceed the predefined limit value, the pulse sequence generating unit 103 is notified that the pulse sequence generating unit 103 is to generate a new pulse sequence PS using new activation parameters. The pulse sequence generating unit 103 transfers the signal amplitude values assigned to the pulse sequence PS, but only those values in the critical region KB (e.g., in the critical pulse sequence segment or the previously determined and now unmodified preserved critical region KB) are transferred to the pulse sequence checking unit 104 or the stimulation value determination unit 105 as a test region. The stimulation value determination unit 105 calculates the stimulation values for the critical region KB only and supplies the stimulation values to the stimulation test unit 106. The simulation test unit 106 checks whether the received stimulation values exceed a predefined limit value. If the received stimulation values do not exceed the predefined limit value, the pulse sequence generating unit is notified accordingly. The pulse sequence generating unit then supplies the approved pulse sequence to the MR scanner or activation unit 107. The stimulation monitoring unit 108 arranged in the MR scanner or activation unit 107 tests in realtime whether the stimulation values STIM assigned to the pulse sequence PS comply with a predefined limit value. If the stimulation values STIM assigned to the pulse sequence PS do not comply with a predefined limit value, a sequence termination is performed. However, if the tested pulse sequence PS is approved, the tested pulse sequence PS is transferred to the pulse sequence amplifier 109, which forwards the tested pulse sequence PS to the gradient coils (not shown).

Figure 2:
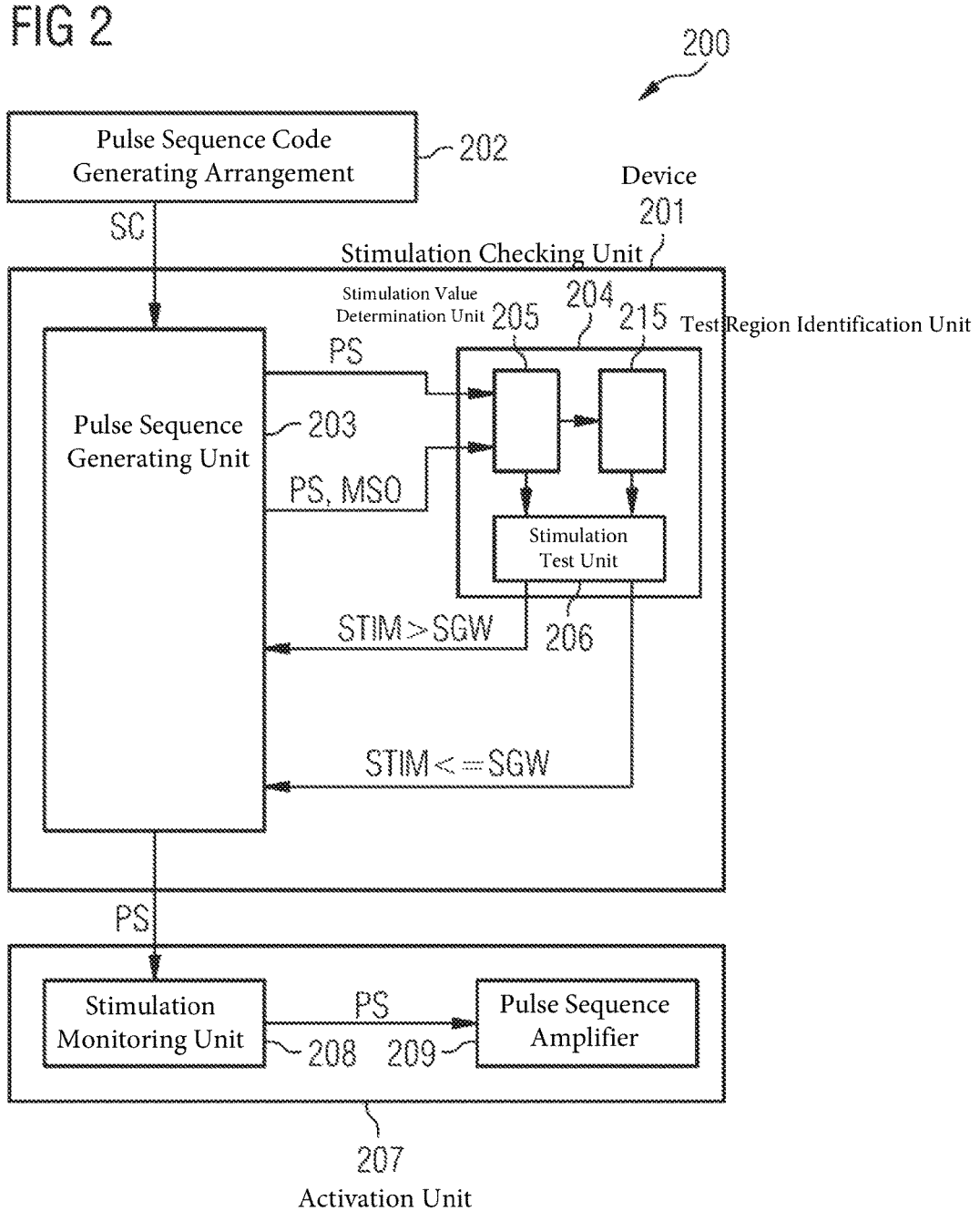
FIG. 2 shows a schematic illustration of one embodiment of a control apparatus.

FIG. 2 shows one embodiment of a control apparatus 200, which includes a device 201 according to an exemplary embodiment for determining activation parameters that are used when activating a magnetic resonance system, and an activation unit 207. The device 201 also includes a pulse sequence code generating arrangement 202, a pulse sequence generating unit 203, a stimulation checking unit 204 and an MR scanner 207 or activation unit 207. However, these are constructed in a manner that is different to the units used in the device according to the prior art, and these also have very different functions, as illustrated in detail below. The pulse sequence code generating arrangement 202 still generates a pulse sequence code SC, but the pulse sequence code generating arrangement 202 does not define critical regions that are subsequently examined more closely by the stimulation checking unit, as per the corresponding unit in FIG. 1. The pulse sequence generating unit 203 generates a pulse sequence PS and supplies the pulse sequence PS (e.g., the whole pulse sequence PS in a specific embodiment variant) to the stimulation checking unit 204. In comparison with the stimulation checking unit 104 in FIG. 1, the structure of the stimulation checking unit 204 is completely different. In addition to a stimulation value determination unit 205 and a stimulation test unit 206, the stimulation checking unit 204 also includes a test region identification unit 215. Unlike the corresponding device 105 in FIG. 1, the stimulation value determination unit 205 determines the stimulation values STIM for not only a predefined critical region of the pulse sequence, but for a wide segment of the pulse sequence (e.g., for the whole of the pulse sequence PS that has been received). Only the test region identification unit 215 defines, based on the determined stimulation values STIM, the pulse sequence segments that are to undergo further examination as critical regions or test regions MSO. The test region identification unit 215 supplies these test regions MSO, or the stimulation values assigned to these test regions MSO, to the stimulation test unit 206. The stimulation test unit 206 tests whether the transferred stimulation values STIM exceed a predefined limit value SGW. If the transferred stimulation values STIM exceed the predefined limit value SGW, the pulse sequence generating unit 203 is notified that it is to generate a new pulse sequence PS using new activation parameters. The pulse sequence generating unit 203 transfers the signal amplitude values assigned to the pulse sequence PS, but only the signal amplitude values in the test region MSO, to the pulse sequence checking unit 204 or the stimulation value determination unit 205. The stimulation value determination unit 205 again calculates the stimulation values, but this time only for the critical region or test region MSO already determined in the previous pass. The stimulation value determination unit 205 supplies these to the stimulation value test unit 206. In this case, the test region or pulse sequence segments in which the stimulation value maxima of the pulse sequence were previously determined, are not determined again. Instead, the stimulation data is transferred directly to the stimulation test unit 206. This tests whether the received stimulation values exceed a predefined limit value. If the stimulation values do not exceed a predefined limit value, the pulse sequence generating unit 203 is notified accordingly. The pulse sequence generating unit 203 then supplies the approved pulse sequence to the MR scanner. Alternatively, the pulse sequence generating unit calculates adapted activation parameters for the pulse sequence based on the predefined stimulation limit value, and sends a pulse sequence that is modified (e.g., optimized with respect to signal amplitude) to the MR scanner. The pulse sequence is, however, still checked by the pulse sequence checking unit 204 before the transfer to the MR scanner 207. The stimulation monitoring unit 208, which is arranged in the MR scanner 207, tests in real time whether the stimulation values STIM assigned to the pulse sequence PS comply with a predefined limit value SGW. If the stimulation values STIM assigned to the pulse sequence PS do not comply with a predefined limit value SGW, a sequence termination is performed. However, if the tested pulse sequence PS is approved, the tested pulse sequence PS is transferred to the pulse sequence amplifier 209, which forwards the tested pulse sequence PS to the gradient coils (not shown).

Figure 3:
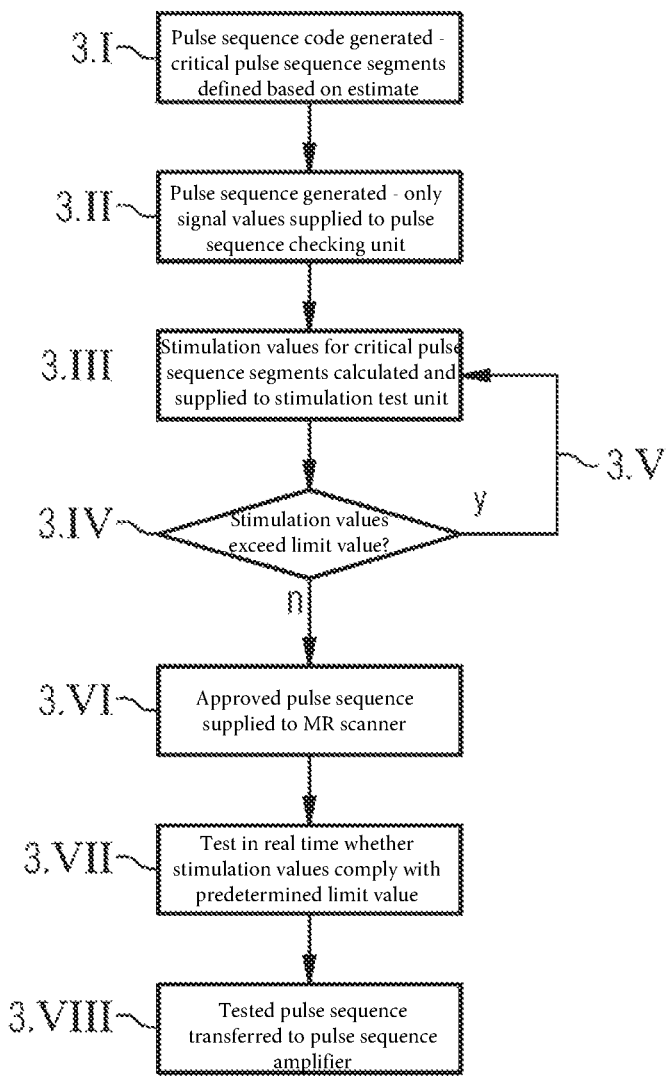
FIG. 3 shows a flowchart that represents one embodiment of a method for adapting activation parameters used to generate a pulse sequence when activating a magnetic resonance system of the prior art.
Figure 4:
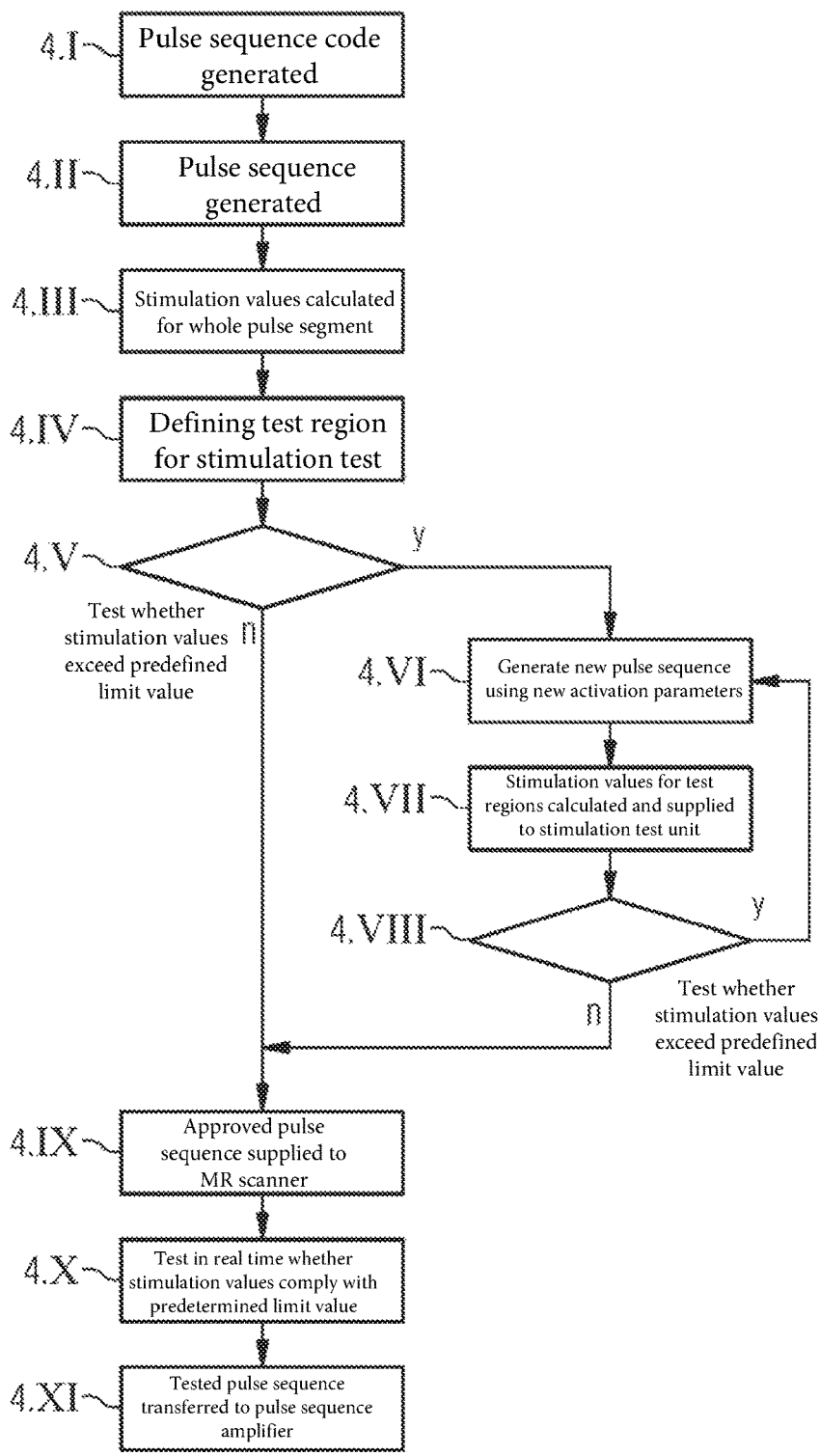
FIG. 4 shows a flowchart that represents a possible execution of one embodiment of a method for adapting activation parameters used to generate a pulse sequence when activating a magnetic resonance system.

In order to allow a detailed understanding of the differences between the method according to one or more of the present embodiments and a conventional method, these are illustrated by flowcharts in FIGS. 3 and 4 for the purpose of comparison.

FIG. 3 shows a conventional method for adapting activation parameters that are used when activating a magnetic resonance system. In act 3.I, a pulse sequence code is generated first, and critical pulse sequence segments that are to subsequently be tested with respect to stimulation values are defined once based on an estimate. In act 3.II, a pulse sequence is generated, and only signal values corresponding to the previously defined critical pulse sequence segments are supplied to the pulse sequence checking unit 104. In act 3.III, only the stimulation values for the cited critical pulse sequence segments are calculated and supplied to the stimulation test unit 106. In act 3.IV, provision is made for testing that the determined stimulation values do not exceed a predefined limit value. If the limit value is exceeded, as indicated by "y" in FIG. 3, a return to act 3.II is effected. More precisely, a new pulse sequence PS is generated using new activation parameters in act 3.II, and again only those signal values STIM corresponding to the critical pulse sequence segments KB are supplied to the pulse sequence checking unit. The acts 3.III and 3.IV are then executed again. If the limit value is not exceeded this time when testing whether the determined stimulation values exceed a predefined limit value SGW, as indicated by "n" in FIG. 3, the approved pulse sequence PS is then supplied to the MR scanner in act 3.V. In act 3.VI, provision is made for testing in real time whether the stimulation values STIM assigned to the pulse sequence PS comply with a predefined limit value SGW. If the stimulation values STIM assigned to the pulse sequence PS do not comply with a predefined limit value SGW, a sequence termination is performed. However, if the tested pulse sequence PS is approved, the tested pulse sequence PS is transferred in act 3.VII to the pulse sequence amplifier 109, which forwards the tested pulse sequence PS to the gradient coils (not shown)

FIG. 4 illustrates the method for adapting activation parameters that are used to generate a pulse sequence when activating a magnetic resonance system in accordance with an exemplary embodiment. This differs significantly from the conventional method shown in FIG. 3.

In act 4.I, a pulse sequence code SC is generated first. Unlike act 3.I in FIG. 3, no critical pulse sequence segments that are to subsequently be tested with respect to corresponding stimulation values are defined once based on an estimate. In act 4.II, a pulse sequence PS is generated. Unlike act 3.II in FIG. 3, not only those signal values corresponding to the critical pulse sequence segments are supplied to the pulse sequence checking unit 204, but instead a considerably larger portion of the pulse sequence PS or the signal values corresponding to this portion (e.g., the whole pulse sequence or the signal values assigned to the whole pulse sequence) is transferred to the stimulation checking unit 204. In act 4.III, not only the stimulation values STIM for the cited critical pulse sequence segments are determined or calculated and supplied to the stimulation test unit, as occurs in act 3.III in FIG. 3; in act 4.III, the stimulation values STIM are determined or calculated for the greater part of a pulse segment (e.g., the whole pulse segment), which is supplied to the stimulation checking unit 204. The determined stimulation values STIM are not then supplied directly to the stimulation test unit 206, but are first transferred to a test region identification unit 215. The determination of the stimulation values may be performed such that a stimulation curve is determined or calculated for the generated pulse sequence. Alternatively, however, a smaller number of stimulation values may be determined (e.g., one or two values in the extreme case). In act 4.IV, provision is made for defining the critical region or test region MSO for which a stimulation test is to be performed. In complete contrast to the act 3.I in FIG. 3, this is not now effected by heuristic estimation, but directly based on the stimulation values STIM determined in act 4.III. For example, the regions with the highest stimulation values or the stimulation maxima are identified. In act 4.V, provision is made for testing, with regard to the determined test region MSO, whether the determined stimulation values STIM exceed a predefined limit value SGW. If the limit value SGW is exceeded, as indicated by "y" in FIG. 4, a return to, for example, act 4.II is not now effected. On the contrary, provision is made in act 4.VI for generating a new pulse sequence PS using new activation parameters in a similar manner to act 4.II and, for example, based on a proposal calculation. Only those pulse signal values corresponding to the determined test regions MSO or the determined test region MSO are supplied to the pulse sequence checking unit. For example, a segment-based modification of the pulse sequence may be performed in only one test region, and only one pulse sequence segment that is assigned to this test region may be transferred to the pulse sequence checking unit. In act 4.VII, only the stimulation values STIM for the already determined test regions MSO or the already determined test region MSO are calculated, and the stimulation values STIM are supplied directly to the stimulation test unit 206. In act 4.VIII, the stimulation test unit 206 tests whether the determined stimulation values STIM exceed a predefined limit value SGW. If, when testing whether the determined stimulation values STIM exceed a predefined limit value SGW, the limit value is still exceeded, a return to act 4.VI is effected, and acts 4.VII and 4.VIII are then executed. If when testing whether the determined stimulation values STIM exceed a predefined limit value SGW in act 4.VIII, the limit value is no longer exceeded, as indicated by "n" in FIG. 4, the approved pulse sequence PS is supplied to the MR scanner 207 in act 4.IX. If it is already determined in act 4.V that the determined stimulation values no longer exceed the limit value SGW, an advance to act 4.IX is already effected. Alternatively, adapted activation parameters for the pulse sequence PS may also be calculated in act 4.IX based on the predefined stimulation limit value SGW, and a modified (e.g., optimized with respect to signal amplitude) pulse sequence is sent to the MR scanner 207. In act 4.X, provision is made for testing in real time whether the stimulation values STIM assigned to the pulse sequence PS comply with a predefined limit value. If the stimulation values STIM assigned to the pulse sequence PS do not comply with a predefined limit value, a sequence termination is performed. However, if the tested pulse sequence PS is approved, the tested pulse sequence PS is transferred in act 4.XI to the pulse sequence amplifier 209. The pulse sequence amplifier 209 forwards the tested pulse sequence PS to the gradient coils. In contrast with the conventional method, therefore, a type of two-stage calculation and determination model is applied. In contrast with the conventional method outlined in FIG. 3, the identification of subregions or subregions of the pulse sequence segments that are crucial for the subsequent calculation is not performed until after the determination of the stimulation values STIM assigned to the pulse sequence PS. Once the test regions MSO that are used in comparison with the method in FIG. 3 have been determined, the subsequent proposal calculation or the subsequent test acts are only performed on the test regions MSO, these being very narrow in comparison with the segments KB that are statically defined beforehand in FIG. 3, thereby accelerating the method and consequently reducing the total time of the image recording method. The convenience for the operator is therefore significantly improved. The stimulation checking becomes considerably more accurate and reliable, since the probability that the selected test regions MSO are incorrect or do not contain the stimulation maximum is greatly reduced or is eliminated almost completely in the event that the stimulation values are determined by calculation based on a detailed model. The probability of unnecessary sequence terminations may therefore be considerably reduced. The tolerance limits for the signal amplitude or the corresponding activation parameters of the generated pulse sequence may be significantly reduced, because the selection of the test region is far more reliable than is the case when using the conventional method.

Figure 5:
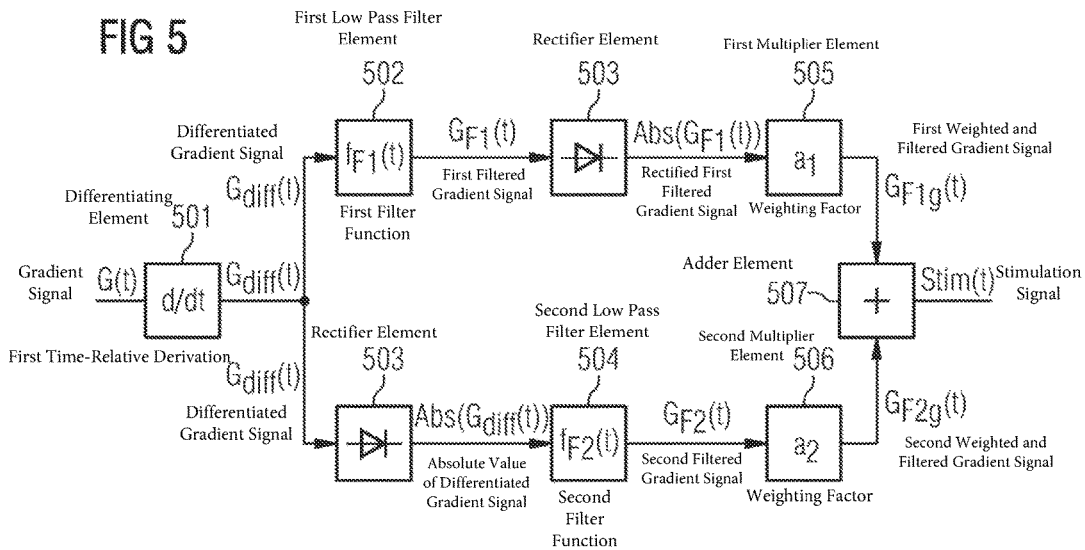
FIG. 5 shows an illustration of an arithmetic realization of an exemplary method act for determining the stimulation values.

FIG. 5 shows a flowchart that illustrates a possible method for determining the stimulation values assigned to the pulse sequence that has been generated. In this case, the stimulation values are calculated according to the following formula:

$$Stim(t) = a_1 \cdot abs\left(\frac{d}{dt}G(t) \otimes f_{F1}(t)\right) \oplus a_2 \cdot abs\left(\frac{d}{dt}G(t)\right) \otimes f_{F2}(t)$$

In this case, Stim(t) is the stimulation function to be determined, G(t) is the gradient signal, d/dt G(t) is the first time-relative derivation of the gradient signal, subsequently also referred to as $G_{diff}(t)$, $f_{F1}(t)$ is a first filter function, $f_{F2}(t)$ is a second filter function, and $a_1$ and $a_2$ are weighting factors. The operator $\otimes$ is a convolution operator, and the operator $\oplus$ represents a composition. According to an embodiment, the composition may be an addition. The diagram suggests a hardware-based system. The flowchart, however, is merely intended to illustrate the computing method, and a software solution (e.g., the use of a computer program) may be provided for the purpose of calculating the stimulation values in the stimulation checking unit.

The flowchart includes a differentiating element 501, to which a measured gradient signal G(t) is supplied. For the sake of simplicity, the computing method is explained with reference to a trapezoidal gradient signal.

Figure 6:
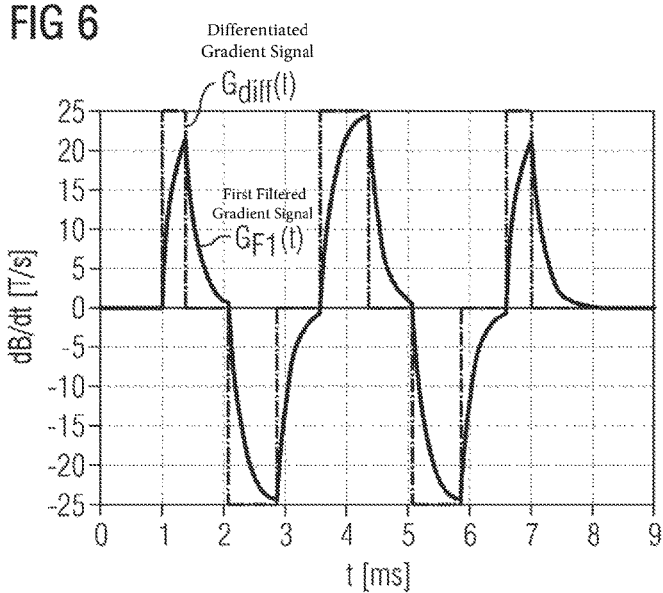
FIG. 6 graphically illustrates an exemplary differentiated gradient signal $G_{diff}(t)$ and a filtered gradient signal $G_{F1}(t)$.

In the differentiating element 501, a differentiated gradient signal $G_{diff}(t)$, with a time-relative profile that is shown in FIG. 6, is formed from the gradient signal G(t) using a first time-relative derivation d/dt. The differentiated gradient signal $G_{diff}(t)$ is passed to a first low-pass filter element 502 and a second low-pass filter element 504. By way of example, both low-pass filter elements 502, 504 are arranged in parallel and connected downstream of the differentiating element 501. A rectifier element 503 is connected downstream of the first low-pass filter element 502, and a rectifier element 503 is connected upstream of the second low-pass filter element 504, whereby only the rectified portion of the differentiated gradient signal $G_{diff}(t)$ is supplied to the second low-pass filter element 504. This provides that only the absolute value of the differentiated gradient signal $G_{diff}(t)$ is available for the subsequent signal processing. In the first low-pass filter element 502, the differentiated gradient signal $G_{diff}(t)$ is filtered using a first filter function $f_{F1}(t)$. In the second low-pass filter element, the absolute value of the differentiated gradient signal $G_{diff}(t)$ is filtered using a second filter function $f_{F2}(t)$.

For example, the filter functions $f_{F1}(t)$ and $f_{F2}(t)$ may be defined as follows:

$$f_{F1}(t)=1/\tau_1 * e^{-t/\tau_1} \text{ and } f_{F2}(t)=1/\tau_2 * e^{-t/\tau_2}$$

with the time constants $\tau_1$ and $\tau_2$.

The following expression is produced for the filtered differentiated gradient signal $G_{F1}(t)$:

$$G_{F1}(t) = G_{diff}(t) \otimes \frac{1}{\tau_1} e^{\frac{-t}{\tau_1}} = \frac{1}{\tau_1} \int_{-\infty}^{+\infty} G_{diff}(t_1) \cdot e^{\frac{-(t-t_1)}{\tau_1}} dt_1$$

The following expression is produced for the filtered differentiated gradient signal $G_{F2}(t)$:

$$G_{F2}(t) = \text{abs}(G_{diff}(t)) \otimes \frac{1}{\tau_2} e^{\frac{-t}{\tau_2}} = \frac{1}{\tau_2} \int_{-\infty}^{+\infty} \text{abs}(G_{diff}(t_2) \cdot e^{\frac{-(t-t_2)}{\tau_2}} dt_2$$

The filtering of the differentiated gradient signal $G_{diff}(t)$ using a first filter function $f_{F1}(t)$, and of a rectified portion $\text{abs}(G_{diff}(t))$ using a second filter function $f_{F2}(t)$, approximately describes the stimulations caused by an external electric field and onward transfer in the nervous system. In this context, the first filter function $f_{F1}(t)$ describes the excitation of the action potential on the pre-synaptic side, resulting in the spilling out of chemical messenger substances (e.g., neurotransmitters). These messenger substances are absorbed on the post-synaptic side (e.g., in the next nerve cell) and trigger a further action potential there. The excitation of the action potential on the post-synaptic side is described by the filter function $f_{F2}(t)$. Since the original polarity of the excitation is no longer contained in the action potential on the post-synaptic side, only the rectified portion of the differentiated gradient signal $G_{diff}(t)$, designated by $\text{abs}(G_{diff}(t))$, is processed in the second low-pass filter element 504. The filtering of the differentiated gradient signal $G_{diff}(t)$ in the first low-pass filter element 502 therefore depicts the pre-synaptic behavior as a model. The time-relative profile of the first filtered gradient signal is illustrated in FIG. 6, where $\tau_1=0.2$ ms is selected for the first time constant. The differentiated gradient signal $G_{diff}(t)$ is also marked in FIG. 6 for the purpose of comparison. The time-relative profile of the second filtered gradient signal $G_{F2}(t)$ is illustrated in FIG. 7, where $\tau_2=2.0$ ms is selected for the second time constant. The absolute value of the differentiated gradient signal $G_{diff}(t)$, designated by $\text{abs}(G_{diff}(t))$, is also marked in FIG. 7 for the purpose of comparison. Both the first filtered gradient signal $G_{F1}(t)$ and the second filtered gradient signal $G_{F2}(t)$ are given respective weightings in a subsequent method act. For example, this may be done by multiplying the rectified first filtered gradient signal $\text{Abs}(G_{F1}(t))$ with a predefinable first weighting factor $a_1$, and multiplying the second filtered gradient signal $G_{F2}(t)$ by a predefinable second weighting factor $a_2$. In order to achieve this, the first filtered gradient signal $G_{F1}(t)$ is supplied to a first multiplier element 505, and the second filtered gradient signal $G_{F2}(t)$ is supplied to a second multiplier element 506. With respect to the weighting factors $a_1$ and $a_2$, it is the case that $a_1+a_2=1$. A weighted and filtered gradient signal $G_{F1g}(t)=a_1*\text{abs}(G_{F1}(t))$ is therefore determined in the first multiplier element 505. Similarly, a second weighted and filtered gradient signal $G_{F2g}(t)=a_2*\text{abs}(G_{F2}(t))$ is determined in the second multiplier element 506. The two weighted and filtered gradient signals $G_{F1g}(t)$ and $G_{F2g}(t)$ are composed using a freely selectable composition operator $\oplus$ to form a stimulation signal $\text{Stim}(t)$. For example, the composition may be performed by adding the two weighted and filtered gradient signals $G_{F1g}(t)$ and $G_{F2g}(t)$. In order to achieve this, the two weighted and filtered gradient signals $G_{F1g}(t)$ and $G_{F2g}(t)$ are supplied to an adder element 507. The resulting stimulation signal $\text{Stim}(t)$ or the resulting stimulation function is illustrated in FIG. 8. The absolute value of the differentiated gradient signal $G_{diff}(t)$, designated by $\text{abs}(G_{diff}(t))$ is also marked in FIG. 8 for the purpose of comparison.

In the acts that tests whether a stimulation limit value is observed, or whether stimulation occurs at all, it is advantageous to consider the stimulation values in all three spatial directions as per the gradients $G_x$, $G_y$ and $G_z$. In this case, for example, stimulation threshold values or limit values $\text{Stim}_{lim,x}$, $\text{Stim}_{lim,y}$, $\text{Stim}_{lim,z}$ may be defined for the individual dimensions, and a quotient $\text{Stim}_x(t)/\text{Stim}_{lim,x}$, $\text{Stim}_y(t)/\text{Stim}_{lim,y}$ or $\text{Stim}_z(t)/\text{Stim}_{lim,z}$ is determined for each gradient axis. A composition of the cited quotients is formed. The value determined thereby is compared with a stimulation factor $\text{Stim}_{factor}$ or stimulation limit value, and the presence of stimulation or whether a stimulation limit value has been exceeded may be inferred. The composition or the inequation used for the cited comparison may take the following form:

$$\sqrt{\left(\frac{\text{Stim}_x(t)}{\text{Stim}_{lim,x}}\right)^2 + \left(\frac{\text{Stim}_y(t)}{\text{Stim}_{lim,y}}\right)^2 + \left(\frac{\text{Stim}_z(t)}{\text{Stim}_{lim,z}(t)}\right)^2} < \text{Stim}_{factor}$$

Figure 9:
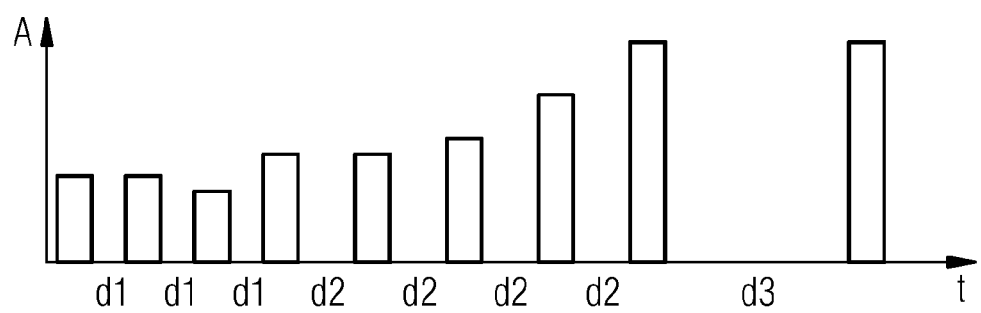
FIG. 9 graphically illustrates an exemplary series of gradient pulses having different amplitudes as a function of the time.
Figure 10:
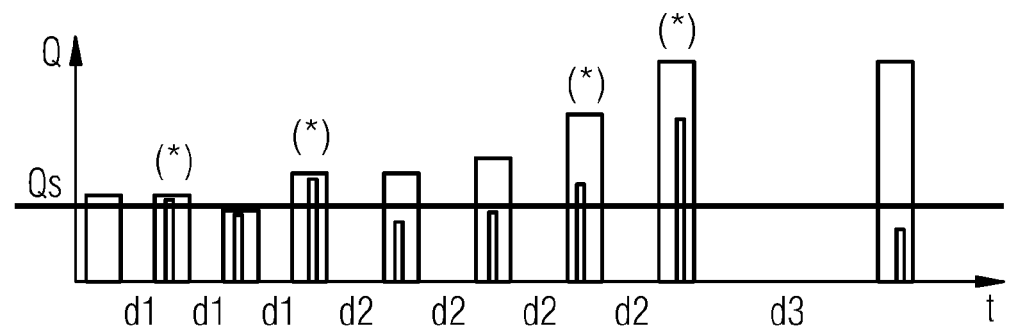
FIG. 10 illustrates a variant for determining the stimulation values of a pulse sequence.

An effective procedure for determining the stimulation values is illustrated in FIGS. 9 and 10. In FIG. 9, the individual gradient pulses having the amplitude A of a pulse sequence are plotted at a time interval d. FIG. 10 illustrates how to decide on the pulses for which the stimulation values are to be determined. The time intervals d ($d=d_1$, $d_2$, $d_3$) between the individual pulses of the whole pulse sequence, and the amplitudes d of the individual pulses of the whole pulse sequence, are determined. The quotients $Q=A/d$ are then calculated from the time intervals and the amplitude of the respective pulse sequence. If the determined quotients Q exceed a limit value $Q_S$, it is to be assumed that stimulation applies for these pulses. These pulses are identified by (*) in FIG. 10. The stimulation caused by these pulses is then to be calculated in accordance with the method outlined in FIG. 5, for example.

The present embodiments offer effective possibilities for providing an improved method and a corresponding device for adapting activation parameters that are used when activating a magnetic resonance system. In this context, the method may be implemented in the form of a software solution and as hardware (e.g., one or more processors). The acts 4.I to 4.IX may be implemented as software, while the acts X and X1 may be embodied as an arrangement that is implemented at least partly in the form of hardware.

The features of all exemplary embodiments or developments disclosed in the figures may be used in any desired combination.

The detailed methods and designs described above relate to exemplary embodiments, and the underlying principle may also be varied extensively by a person skilled in the art without thereby departing from the scope of the invention as specified by the claims. The indefinite article "a" or "an" does not exclude the possibility of multiple occurrences of the features concerned. The term "unit" or "module" does not exclude the possibility of this including a plurality of components, which may also be physically distributed if applicable.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for adapting activation parameters that are used to generate a pulse sequence when activating a magnetic resonance system, the method comprising:
   determining, by the magnetic resonance system, stimulation values for the pulse sequence based on predefined activation parameters, the stimulation values representing a stimulation exposure of a patient;
   identifying test regions of the pulse sequence based on the stimulation values;
   testing the identified test regions with respect to compliance with a predefined stimulation limit value; and
   imaging, by the magnetic resonance system, the patient applying the pulse sequence when the testing indicates that the stimulation values for the pulse sequence comply with the predefined stimulation limit value.

2. The method of claim 1, wherein the predefined stimulation limit value is a first predefined stimulation limit value, and
   wherein when the stimulation limit value is exceeded in a test region, the method further comprises:
   generating, using new activation parameters, a modified pulse sequence for at least the test region;
   determining the stimulation values for the modified pulse sequence in the test region; and
   testing the test region with respect to compliance with a second predefined stimulation limit value.

3. The method of claim 2, further comprising:
   performing a proposal calculation of the activation parameters based on the predefined stimulation limit value and the stimulation values that have been determined for the identified test regions; and
   generating the new activation parameters, the performing of the proposal calculation being before the generating of the new activation parameters.

4. The method of claim 2, further comprising supplying the determined activation parameters to an activation unit of the magnetic resonance system when the determined stimulation values do not exceed the second predefined limit value.

5. The method of claim 1 wherein determining the stimulation values comprises calculating values representing the stimulation based on the pulse sequence.

6. The method of claim 5, wherein calculating the values representing the stimulation comprises:
   calculating a first derivation of the pulse sequence;
   calculating a first filtered gradient signal by convolution of the first derivation of the pulse sequence with a first filter function;
   calculating absolute values of the first filtered gradient signal of the pulse sequence;
   calculating absolute values of the first derivation;
   calculating a second filtered gradient signal by convolution of the absolute values of the first derivation with a second filter function;
   weighting the first filtered gradient signal with a first weighting factor and weighting the second filtered gradient signal with a second weighting factor; and
   composing the first weighted filtered gradient signal and the second weighted filtered gradient signal to form a stimulation function.

7. The method of claim 1, wherein determining the stimulation values comprises:
   determining time intervals between individual pulses of the pulse sequence;
   determining amplitudes of the individual pulses of the pulse sequence;
   determining quotients from the time intervals and the amplitudes of the respective pulse sequence;
   determining which of the quotients exceed a limit value; and
   determining the stimulation values for only the pulses assigned to the determined quotients.

8. The method of claim 1, wherein determining the stimulation values comprises:
   determining time intervals between individual pulses of the pulse sequence;
   defining test regions in pulse sequence segments where a predefined minimal time interval between two pulses is not reached; and
   determining the stimulation values for only the defined test regions.

9. The method of claim 8, wherein the predefined minimal time interval is determined as a function of a maximal time-relative change in gradient pulses of the pulse sequence.

10. A device for determining activation parameters that are used when activating a magnetic resonance system, the device comprising:
    a pulse sequence generating unit configured to generate a pulse sequence;
    a processor configured to:
        determine stimulation values for the pulse sequence based on predefined activation parameters, the stimulation values representing a stimulation exposure of a patient;
        determine test regions based on the stimulation values of the pulse sequence; and
        verify the determined test regions with respect to compliance with a predefined stimulation limit value; and an activation unit configured to initiate imaging of the patient by the magnetic resonance system, wherein when the verifying indicates that the stimulation values for the pulse sequence comply with the predefined stimulation limit value, the pulse sequence generating unit transfers the pulse sequence to the activation unit and the activation unit initiates imaging of the patient by the magnetic resonance system applying the pulse sequence.

11. The device of claim 10, wherein the pulse sequence generating unit is further configured to:

when the predefined stimulation limit value is not observed, generate a new pulse sequence using new activation parameters and supply only pulse sequence segments in the determined test region to a stimulation checking unit.

12. The device of claim 11, wherein the processor is further configured to:

determine, when the stimulation limit value is exceeded, the stimulation values for a pulse sequence that has been newly generated by the pulse sequence generating unit using new activation parameters for the determined test regions; and test the determined test regions again with respect to compliance with the predefined stimulation limit value.

13. The device of claim 10, wherein the processor is further configured to perform, before the generation of the new activation parameters, a proposal calculation of the activation parameters based on the predefined stimulation limit value and the stimulation values that have been determined for the determined test regions.

14. A controller comprising:

a device for determining activation parameters that are used when activating a magnetic resonance system, the device comprising:

a processor configured to:

determine stimulation values for a pulse sequence based on predefined activation parameters, the stimulation values representing a stimulation exposure of a patient;

determine test regions based on the stimulation values of the pulse sequence; and verify the determined test regions with respect to compliance with a predefined stimulation limit value; and a pulse sequence code generating unit configured to generate a pulse sequence code for a pulse sequence generating unit without defining critical regions for stimulation testing, wherein when the verifying indicates that the stimulation values for the pulse sequence comply with the predefined stimulation limit value, the patient is imaged by the magnetic resonance system applying the pulse sequence.

15. A magnetic resonance tomography system comprising:

a device for determining activation parameters that are used when activating a magnetic resonance system, the device comprising:

a processor configured to:

determine stimulation values for a pulse sequence based on predefined activation parameters, the stimulation values representing a stimulation exposure of a patient;

determine test regions based on the stimulation values of the pulse sequence; and verify the determined test regions with respect to compliance with a predefined stimulation limit value, wherein when the verifying indicates that the stimulation values for the pulse sequence comply with the predefined stimulation limit value, the patient is imaged by the magnetic resonance system applying the pulse sequence.

* * * * *